United States Patent [19]
Felder et al.

[11] 4,165,630
[45] Aug. 28, 1979

[54] CONTINUOUS IN-STACK POLLUTANT MONITORING SYSTEM

[75] Inventors: Richard M. Felder; James K. Ferrell, both of Raleigh, N.C.

[73] Assignee: North Carolina State University at Raleigh, Raleigh, N.C.

[21] Appl. No.: 815,553

[22] Filed: Jul. 14, 1977

[51] Int. Cl.² ............................................. G01N 31/00
[52] U.S. Cl. .................................... 73/23; 73/421.5 A
[58] Field of Search ...................... 73/23, 421.5 A, 24, 73/25, 26

[56] References Cited
U.S. PATENT DOCUMENTS

| | | | |
|---|---|---|---|
| 3,924,442 | 12/1975 | Kerho et al. | 73/23 X |
| 3,976,450 | 8/1976 | Marcote et al. | 73/23 X |

Primary Examiner—Jerry W. Myracle
Attorney, Agent, or Firm—Mills & Coats

[57] ABSTRACT

In abstract a preferred embodiment of the present invention is a pollutant monitoring system designed to continuously monitor and record the concentration level of a particular pollutant in a stack. The present invention incorporates an in-stack interface to condition gas samples and a microprocessor to automatically and continuously compute the pollutant level found within a stack by using input variables supplied by probes and meters located throughout the pollutant monitoring system. The microprocessor then outputs the computed pollutant levels to a strip chart recorder which in turn graphs a time versus concentration readout.

11 Claims, 2 Drawing Figures

CONTINUOUS IN-STACK POLLUTANT MONITORING SYSTEM

The present invention relates to a pollutant monitoring device and more particularly to an in-stack pollutant monitoring system which incorporates an in-stack permeable interface with automatic temperature compensation and automatic carrier gas flow rate compensation for continuously monitoring and recording the concentration level of a particular pollutant.

BACKGROUND OF THE INVENTION

Stack gas analysis has traditionally been performed by drawing a sample through a small tube inserted in the stack, collecting and fixing the pollutant in a solution or on a solic by absorption or reaction, and using conductimetric, colorimetric, or photometric analysis to determine the concentration of the pollutant. Some of the techniques in current use are described in "Standards of Performance for New Stationary Sources," *Federal Register*, 36, 24890 (Dec. 23 1971), the Los Angeles Air Pollution Control District "Source Sampling Manual," (1963), and by Cooper and Rossano in "Source Testing for Air Pollution Control," McGraw-Hill, New York, N.Y., 1971. More recently, methods have been developed which provide continuous records of pollutant concentrations. A review of instrumentation for continuous $SO_2$ monitoring has been compiled by Hollowell et al in *Analytical Chemistry*, 45, 63A (1973).

A gas sample withdrawn directly from a stack must usually be conditioned before passing to a continuous analyzer or a wet chemical sampling train. The conditioning entails removing condensable vapors, mists, solid particulates, and chemical species known to interfere with the analysis of the desired pollutant. A typical sample-conditioning procedure might involve heating the gas to maintain vapors above their dew point or cooling to condense and remove the vapors from the sample stream, filtering the sample to remove particulates, and bubbling the gas through a liquid solution which removes the undesired chemical species but allows the pollutant to pass through to the analyzer.

A. O'Keeffe of the National Environmental Research Center, EPA, proposed using a polymer tube as an in situ stack sampling interface around 1972. In this proposed method, a carrier gas would pass continuously through a polymer tube mounted in the stack, and the pollutant would permeate the tube wall from the stack into the carrier gas stream, which would then pass to a continuous ambient analyzer. This method has several potential advantages over traditional sample conditioning techniques: an average concentration across the stack can be measured, polymers can be used which do not pass interfering pollutants, vapors in the carrier gas stream should be well above their dew points, and particulate filters are not required.

However, there are disadvantages to this system for commercial use. In the first place, the permeability of the interface is a function of temperature. Thus, the temperature must be recorded and the readings of the gas analyzer corrected for variations in this variable. Secondly, the pollutant concentration as measured by the gas analyzer is a function of the carrier gas flow rate. Thus, the flow rate must be kept constant or, alternatively, measured and the gas analyzer readings corrected for fluctuations in this variable.

It is the purpose of the present invention to provide a system which eliminates the disadvantages associated with current methods of stack gas monitoring and provides a continuous gas pollutant monitor having commercial attributes. It incorporates the idea of using a permeable interface for in situ stack sampling proposed by O'Keeffe. The inventors are the only ones who have developed and demonstrated the feasibility of the technique. The concept of the interface was described in *Environmental Science and Technology*, 7 545 (1973) and 10, 457 (1976). The complete apparatus, and most particularly the automatic temperature and flow rate compensation which are integral to the commercial viability of the device, is the subject of the current invention.

The only related invention disclosed by a patent search is a gas dilution apparatus, U.S. Pat. Nos. 3,833,016 (Sept. 3, 1974), assigned to Meloy Laboratories, Inc., of Springfield, Va. Like the present invention, the Meloy device uses a membrane to dilute a stack gas prior to analysis. However, the Meloy device is an out-of-stack sampler: a gas sample is withdrawn from the stack and contacts the membrane externally in a heated chamber. Contamination due to condensation, pollutant sorption, and particulate buildup—the problems the present invention is designed to overcome—are not eliminated by the Meloy device. The in situ method of calibration and operation, the cross-section averaged sampling, the flexibility in handling a wide range of stack pollutant levels and temperatures, and the data logging and analysis features of the present invention provide substantial advances in the state of the art over the Meloy apparatus.

SUMMARY OF THE INVENTION

The present invention consists of a permeable in-stack interface in combination with continuous gas analysis, permeable interface temperature measurement, and carrier gas flow-rate measurement, all data being manipulated by a microprocessor to effectively and continuously monitor stack pollutant concentration.

The purpose of the permeable interface is to condition gas samples prior to analysis, providing samples that are free of particulate matter and contain water in quantities low enough to preclude the possibility of condensation in the gas line or analyzer, and contain the pollutant in a concentration proportional to the concentration in the stack and within the operating range of the analyzer to be used. In addition, the present invention incorporates automatic temperature and carrier gas flow-rate compensation. In combination, the system is intended to permit continuous stack gas pollutant monitoring for long periods of time unattended except for occasional recalibration.

In view of the above, it is an object of the present invention to provide an in-stack pollution monitoring system which continuously monitors and records stack gas pollutant concentrations.

Another object of the present invention is to provide an in-stack pollution monitoring system which utilizes a permeable in-stack interface to effectively condition gas samples.

Another object of the present invention is to provide an in-stack pollution monitoring system whose permeable interface is constructed of Teflon type plastic or any other material which is permeable to the species to be monitored.

Another object of the present invention is to provide an in-stack pollution monitoring system which incorporates a carrier gas system whereby pollution samples which permeate through the interface may be readily and continuously carried out of the stack and into the gas analyzer.

Another object of the present invention is to provide an in-stack pollution monitoring system which incorporates a microprocessor for continuously computing pollution concentration levels after having received data regarding the sample gas from a gas analyzer, a temperature measuring device, and a carrier gas flow meter.

Another object of the present invention is to provide an in-stack pollution monitoring system which incorporates an in-situ calibration system for readily calibrating the pollution monitoring system.

Another object of the present invention is to provide an in-stack pollution monitoring system which outputs a continuous time versus pollutant concentration record.

Other objects and advantages of the present invention will become apparent from a study of the following description and the accompanying drawings which are illustrative of the present invention.

DETAILED DESCRIPTION OF THE PREFERRED EMBODIMENT

Figure 1:
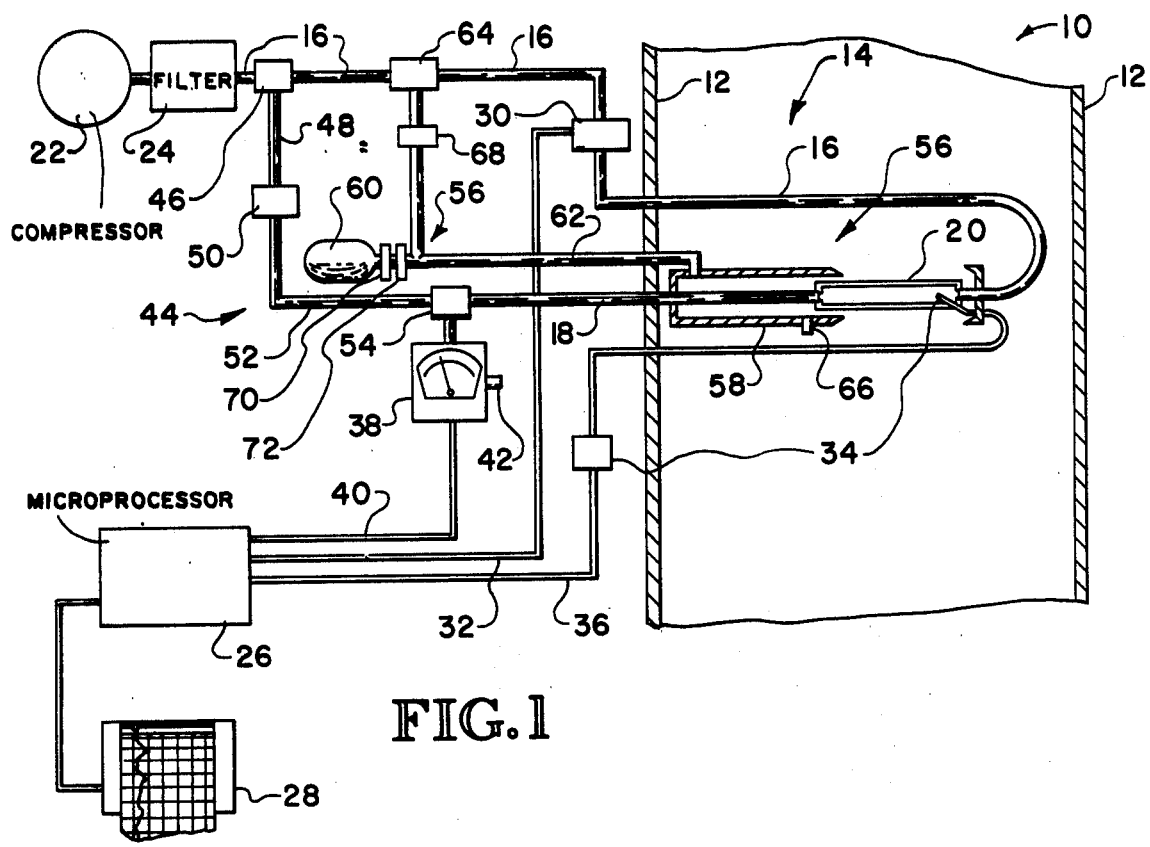
FIG. 1 is a schematic diagram of the present invention illustrating the in-stack pollution monitoring system in the normal monitoring mode.

With further reference to the drawings, particularly FIG. 1, an in-stack pollution monitoring system is shown therein and indicated generally by the numeral 10. In-stack pollution monitoring system 10 comprises an interface portion indicated generally by the numeral 14 which is disposed within the interior of stack 12. Interface portion 14 is comprised of a permeable interface 20 which connects carrier gas inlet line 16 to a carrier gas outlet line 18 such that carrier gas flowing from inlet line to outlet line must pass within the interior of interface 20. The carrier gas is supplied to interface portion 14 by a compressor 22 and an in-line filter 24. The carrier gas may be air or any other gas which will not interfere with the measurement of the desired pollutant.

A microprocessor 26 and its associated strip chart recorder 28 are communicatively connected to three data sensors appropriately located in the pollution monitoring system. One such sensor is carrier gas mass flow meter 30 which is attached to carrier gas inlet line 16 to monitor carrier gas flow and transmit data pertaining to the same back to the microprocessor via data transmitting line 32.

Another such sensor is the temperature measuring device 34 which is incorporated within the interface portion 20 to sense carrier gas temperature within the permeable interface 20. The temperature sensing device 34 is connected to microprocessor 26 by a data transmitting line 36. Carrier gas outlet line 18 directs pollutant-containing carrier gas to the third sensor which is gas analyzer 38. The gas analyzer 38, such as the commercially sold Meloy Labs Model SA-160 Sulfur Gas Analyzer, continuously evalutes the concentration level of pollutant within the carrier gas and transmits such data to microprocessor 26 via data transmitting line 40. Gas analyzer 38 incorporates a vent 42 to expel the analyzed carrier gas from the system.

Incorporated within the in-stack pollution monitoring system 10 is a gas analyzer calibration system generally indicated by the numeral 44. Gas analyzer calibration system 44 comprises a valving means 46 to direct carrier gas into the calibration system 44 where known concentrations of the pollutant being measured are generated by passing the carrier gas across a standard permeation tube 50. This calibration gas is directed to the gas analyzer 38 by line 52 and a valving means 54.

Figure 2:
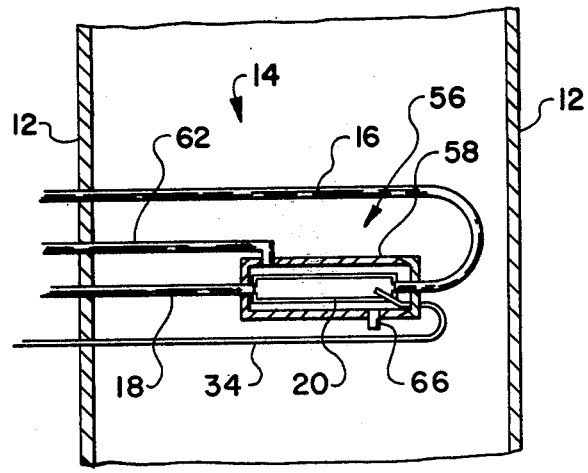
FIG. 2 is a schematic diagram of the present invention illustrating the in-stack monitoring system in the interface calibration mode.

In addition the in-stack pollution monitoring system 10 incorporates an interface calibration system indicated generally by the numeral 56. With reference to FIG. 2, interface portion 14 is shown in the calibration mode. Basically, interface calibration system 56 comprises a sheath 58 which may be positioned to enclose the permeable interface 20. The region between sheath 58 and permeable interface 20 is communicatively connected by line 62 to span gas supply 60. The span gas is a carrier gas containing a known concentration of the pollutant. The area between sheath 58 and permeable interface 20 is also communicatively connected to the interior of stack 12 by a vent 66 such that the span gas may flow about the permeable interface 20 and exit sheath 58. Interface calibration system 56 incorporates a valving means 64 and flow rate meter 68 to direct a known flow of carrier gas to line 62 and a valve 70 and flow rate meter 72 to introduce a known flow rate of span gas, such that the span gas may be diluted to any desirable concentration before entry into the area between sheath 58 and permeable interface 20.

In operation the in-stack pollution monitoring system is initially calibrated. First the gas analyzer is calibrated by valving means 46 being actuated, to thereby direct carrier gas over permeation tube 50 or some other standard, which places a known concentration of pollutant into the carrier gas flow. Valving means 54 then directs the calibration gas into the gas analyzer 38 and a calibration signal is sent by way of 40 to the microprocessor 26.

Next the interface portion 14 of the in-stack pollution monitoring system is calibrated by positioning sheath 58 about the permeable interface 20 thereby sealing off the interface from gases rising within stack 12. Carrier gas which is being continuously supplied by compressor 22 and monitored by flow meter 30 is directed to the permeable interface by carrier gas inlet line 16. Valving means 64 bleeds a known flow of carrier gas into the known flow rate of span gas being supplied from span gas reservoir 60. The diluted span gas of known concentration is then directed through line 62 into the interior of sheath 58, thus passing over the permeable interface 20. Permeation of the pollutant through interface 20 causes the carrier gas flowing within permeable interface 20 to have a pollutant concentration which varies linearly with the pollutant concentration in the span gas passing about its exterior surface. To complete the calibration of interface portion 14, the carrier gas is directed to the gas analyzer 38 by carrier gas outlet line 18. Microprocessor 26 receives data from the flow meter, the gas analyzer and the temperature sensing unit and computes the concentration level of the diluted span gas. If the computer results differ from the known concentration of the diluted span gas, adjustments are made within the system to correct for the inaccuracy.

At this time the in-stack pollution monitoring system is ready to monitor the pollutant concentration in the stack. First, sheath 58 is withdrawn from the permeable interface thereby allowing rising stack gases to flow about the same. Carrier gas, which is supplied by compressor 22, flows through carrier gas inlet line 16 and subsequently through the interior of permeable interface 20. Within permeable interface 20 the carrier gas picks up any pollutant gases which may have permeated through the interface and flows to the gas analyzer 38. Gas analyzer 38 continuously monitors the pollutant concentration in the carrier gas and outputs data via data transmission line 40 to the microprocessor 26. Gas analyzer 38 systematically vents the monitored carrier gas out of the system through vent 42. In addition to gas analyzer data, the microprocessor 26 also receives signals from the carrier gas flow meter 30 and the temperature sensor 34 via data transmission lines 32 and 36, respectively. This information, together with the calibration data obtained earlier, enables the microprocessor to compute the concentration of the pollutant in the stack gas and present a continuous record on chart recorder 28.

For example, the microprocessor of the present invention may be programmed to calculate stack pollutant concentration for any temperature and carrier gas flow rate as follows:

$$C_s = kC_m (Q_m/Q_r) \exp\left[\frac{E(T_r - T_m)}{R\, T_r T_m}\right]$$

where
- $C_s$ = stack gas concentration, ppm
- k = probe calibration constant
- $C_m$ = measured carrier gas concentration, ppm
- $Q_m$ = measured carrier gas flow rate, cc/min
- $Q_r$ = reference carrier gas flow rate, cc/min
- E = activation energy of permeation of interface, (cal/mole)
- R = gas constant, 1.987 (cal/mole) °K.
- $T_r$ = reference temperature, °K.
- $T_m$ = measured temperature, °K.

The microprocessor program first initializes the microprocessor by placing all the parameters required for the calculations into their proper memory locations. The calculations algorithm begins with the sampling of the input signals from the concentration, temperature, and flow sensing devices. The measured conditions are then computed from the sensor calibration data. Once these results have been obtained, the temperature and flow compensation factors can be determined. Finally the stack concentration is calculated and its value is transmitted to a printer or recorder. The computational loop is repeated every second and the results are averaged over a preselected time period to smooth the data. The averaged concentrations are transmitted to the recorder.

It is obvious from the foregoing specification that the present invention overcomes the complicated procedures currently required to obtain stack gas concentrations. It can, therefore, be appreciated that the present invention provides a useful tool to accurately and continuously monitor in-stack pollutant concentration levels.

The present invention, of course, may be carried out in other specific ways than those herein set forth without departing from the spirit and essential characteristics of the invention. The present embodiments are therefore, to be considered in all respects as illustrative and not restrictive, and all changes coming within the meaning and equivalency range are intended to be embraced herein.

What is claimed is:

1. The process of continuously monitoring the concentration of at least one substance within an atmosphere comprising: directing a carrier gas past a permeable interface which is disposed within said atmosphere whereby at least a portion of said substance permeates said interface and becomes homogeneously suspended within said carrier gas; directing said substance containing carrier gas into a gas analyzer; analyzing said carrier gas to determine the concentration of said substance therein; transmitting the concentration data to a microprocessor; measuring the rate of flow of said carrier gas; transmitting the rate of flow data to said microprocessor; measuring the temperature of the carrier gas adjacent the permeable interface; transmitting the measured temperature data to said microprocessor; comparatively evaluating said substance concentration data, said flow rate data, and said temperature data with like determined calibration data previously obtained whereby an accurate, relatively continuous determination of atmosphere concentration of said substance can be obtained.

2. The process of claim 1 wherein in-situ calibration of said permeable interface is periodically performed.

3. The process of claim 2 wherein said in-situ calibration includes a span gas supply of a known substance concentration; and means for directing said span gas adjacent the ambient side of said interface whereby an atmosphere of a known substance concentration is provided for calibration purposes.

4. The process of claim 3 wherein said in-situ calibration system includes a removably positioned closure about said permeable interface whereby ambient atmosphere of unknown substance concentration is blocked out during the calibration process.

5. The process of claim 1 wherein said permeable interface is generally cylindrical in shape with the carrier gas passing longitudinally therethrough.

6. The process of claim 1 wherein the permeable interface is constructed of Teflon.

7. The process of claim 1 wherein said carrier gas is compressed.

8. The process of claim 1 wherein said carrier gas is filtered.

9. The process of claim 1 wherein said carrier gas is compressed and filtered prior to being directed adjacent said permeable interface.

10. The process of claim 1 wherein said permeable interface is disposed within an exhaust stack type atmosphere.

11. The process of claim 1 wherein said substance is sulfur dioxide.

* * * * *